(12) United States Patent
Kaestle et al.

(10) Patent No.: US 10,178,958 B2
(45) Date of Patent: Jan. 15, 2019

(54) DEVICE AND METHOD FOR OBTAINING VITAL SIGN INFORMATION OF A LIVING BEING

(71) Applicants: Siegfried Walter Kaestle, Nuffringen (DE); Caifeng Shan, Eindhoven (NL)

(72) Inventors: Siegfried Walter Kaestle, Nuffringen (DE); Caifeng Shan, Eindhoven (NL)

(73) Assignee: Koninklijke Philips N.V., Eindhoven (NL)

(*) Notice: Subject to any disclaimer, the term of this patent is extended or adjusted under 35 U.S.C. 154(b) by 984 days.

(21) Appl. No.: 14/093,566

(22) Filed: Dec. 2, 2013

(65) Prior Publication Data

US 2014/0155759 A1 Jun. 5, 2014

Related U.S. Application Data

(60) Provisional application No. 61/781,155, filed on Mar. 14, 2013, provisional application No. 61/732,985, filed on Dec. 4, 2012.

(30) Foreign Application Priority Data

Dec. 4, 2012 (EP) .................................... 12195438
Mar. 14, 2013 (EP) .................................... 13159140

(51) Int. Cl.
*A61B 5/11* (2006.01)
*A61B 5/024* (2006.01)
(Continued)

(52) U.S. Cl.
CPC ........ *A61B 5/02427* (2013.01); *A61B 5/0077* (2013.01); *A61B 5/02416* (2013.01);
(Continued)

(58) Field of Classification Search
None
See application file for complete search history.

(56) References Cited

U.S. PATENT DOCUMENTS 5,140,990 A 8/1992 Jones et al.
6,409,654 B1 6/2002 McClain
(Continued)

FOREIGN PATENT DOCUMENTS

CN 1704017 A 12/2005
CN 202437546 U 9/2012
(Continued)

OTHER PUBLICATIONS

Johnston et al., "Extracting Breathing Rate Information from a Wearable Reflectance Pulse Oximeter Sensor," Sep. 1, 2004, Proceedings of the 26th Annual International Conference of the IEEE EMBS, pp. 5388-5391.*

(Continued)

*Primary Examiner* — Tse W Chen
*Assistant Examiner* — Nate Sunwoo

(57) ABSTRACT

A device for obtaining vital sign information of a living being comprises a detection unit that receives light in at least one wavelength interval reflected from at least a region of interest of a living being and that generates an input signal from the received light. A processing unit processes the input signal and derives vital sign information of the living being from the input signal by use of remote photoplethysmography. An illumination unit illuminates at least the region of interest with light, and a control unit controls the illumination unit based on the input signal and/or the derived vital sign information.

12 Claims, 5 Drawing Sheets

(51) Int. Cl.
*A61B 5/1455* (2006.01)
*A61B 5/00* (2006.01)
*A61F 7/00* (2006.01)
*A61G 11/00* (2006.01)

(52) U.S. Cl.
CPC ........ *A61B 5/1128* (2013.01); *A61B 5/14551* (2013.01); *A61B 5/7278* (2013.01); *A61F 7/007* (2013.01); *A61G 11/00* (2013.01); *A61B 2503/045* (2013.01); *A61B 2505/03* (2013.01)

(56) References Cited

U.S. PATENT DOCUMENTS

| | | | |
|---|---|---|---|
| 6,679,830 B2 | 1/2004 | Kolarovic et al. | |
| 6,775,565 B1 | 8/2004 | Wieringa | |
| 2009/0082642 A1* | 3/2009 | Fine | A61B 5/0059 600/300 |
| 2011/0092824 A1* | 4/2011 | Veen | A61B 5/14551 600/477 |
| 2012/0283575 A1 | 11/2012 | Rao et al. | |
| 2014/0243622 A1 | 8/2014 | Crowe et al. | |

FOREIGN PATENT DOCUMENTS

| | | |
|---|---|---|
| DE | 102010056615 A1 | 7/2012 |
| EP | 2438849 A1 | 4/2012 |
| JP | 2009533121 A | 9/2009 |
| RU | 2354290 C1 | 5/2009 |
| RU | 90325 U1 | 1/2010 |
| WO | 2009073396 A1 | 6/2009 |
| WO | 2012093358 A1 | 7/2012 |
| WO | 2012143842 A2 | 10/2012 |
| WO | 2014064575 A2 | 5/2014 |

OTHER PUBLICATIONS

Corral et al., "Optimal wavelength selection for non-contact reflection photoplethysmography," Nov. 2, 2011, Proceedings of SPIE, vol. 8011, 801191, pp. 1-7.*

Verkruysse et al, "Remote Plethysmographic Imaging Using Ambient Light", Opt Express, vol. 16, No. 26, 2008, p. 1-16.

Abbas et al, "Neonatal Non-Contact Respiratory Monitoring Based on Real-Time Infrared Thermography", Bio Medical Engineering Online, vol. 10, No. 93, 2011, p. 1-17.

* cited by examiner

DEVICE AND METHOD FOR OBTAINING VITAL SIGN INFORMATION OF A LIVING BEING

FIELD OF THE INVENTION

The present invention relates to a device and a corresponding method for obtaining vital sign information of a living being.

BACKGROUND OF THE INVENTION

Unobtrusive vital sign monitoring using a video camera, or remote PPG (photoplethysmography), has been demonstrated and found relevant for patient monitoring. Remote photoplethysmographic imaging is, for instance, described in Wim Verkruysse, Lars O. Svaasand, and J. Stuart Nelson, "Remote plethysmographic imaging using ambient light", Optics Express, Vol. 16, No. 26, December 2008. It is based on the principle that temporal variations in blood volume in the skin lead to variations in light absorptions by the skin. Such variations can be registered by a video camera that takes images of a skin area, e.g. the face, while processing calculates the pixel average over a selected region (typically part of the cheek in this system). By looking at periodic variations of this average signal, the heart beat rate and respiratory rate can be extracted. There are meanwhile a number of further publications and patent applications that describe details of devices and methods for obtaining vital signs of a patient by use of remote PPG.

Thus, the pulsation of arterial blood causes changes in light absorption. Those changes observed with a photodetector (or an array of photodetectors) form a PPG (photoplethysmography) signal (also called, among other, a pleth wave). Pulsation of the blood is caused by the beating heart, i.e. peaks in the PPG signal correspond to the individual beats of the heart. Therefore, a PPG signal is a heartbeat signal in itself. The normalized amplitude of this signal is different for different wavelengths, and for some wavelengths it is also a function of blood oxygenation.

Although regular video data have been shown to yield adequate vital signs (sometimes also called biometrical signals, such as heartbeat, respiration rate, SpO2 rate, etc.) in many cases, the image acquisition for challenging cases, like strong motion, low light levels, non-white illumination, needs further improvement. The known methods and devices are generally robust to motion and different lighting environments as long as one dominant light source is present. In such condition the PPG technology has proven to be accurate and robust up to a point that it can be used on a treadmill during fitness exercises.

One major problem encountered in image-based (e.g. camera-based) vital signs monitoring occurs when no dominant light is present in the environment. Further, a particular illumination is not always optimal for all measurements, e.g. for different skin types, body postures or after body movements.

SUMMARY OF THE INVENTION

It is an object of the present invention to provide a device and a corresponding method for obtaining vital sign information of a living being having a higher accuracy and reliability, in particular in situations with changing conditions, compared to known devices and methods.

In a first aspect of the present invention a device for obtaining vital sign information of a living being is presented comprising:
a detection unit that receives light in at least one wavelength interval reflected from at least a region of interest of a living being and that generates an input signal from the received light,
a processing unit that processes the input signal and derives vital sign information of said living being from said input signal by use of remote photoplethysmography,
an illumination unit that illuminates at least said region of interest with light, and
a control unit that controls said illumination unit based on said input signal and/or said derived vital sign information.

In a further aspect of the present invention a corresponding method for obtaining vital sign information of a living being is presented.

Preferred embodiments of the invention are defined in the dependent claims. It shall be understood that the claimed method has similar and/or identical preferred embodiments as the claimed device and as defined in the dependent claims.

Vital signs measurement devices derive vital sign information by measuring the subtle change in the skin area of the region of interest, which in turn relies on the illumination. Normally, a dedicated illumination is needed. However, it has been found that one particular pre-set illumination might not always be optimal for measurement. For example, specular reflection is one of the difficulties, in particular for SpO2 measurement, which should be avoided in the region of interest (ROI) used for measurement. Due to different skin types (conditions) and body postures or after body movement, specular reflections might exist or appear in the ROI. Manually adjusting illumination setup for each measurement, or after each change in the environment or the vital signs measurement device, is subjective and time consuming.

Hence, the present invention proposes an adaptive device and method for unobtrusive vital signs measurement (e.g. heartbeat monitoring, SpO2 monitoring, etc.), which can be automatically configured for optimal measurement. Accordingly, a control unit is provided that controls said illumination unit, e.g. one or more controllable light sources, based on said input signal generated from detected light (reflected from the ROI) and/or the derived vital sign information. Thus, even in case of changing conditions vital sign information can be obtained with optimal accuracy and reliability.

According to a preferred embodiment said control unit is configured to control intensity, wavelength, direction and/or illumination angle of the light emitted by said illumination unit. Dependent on the conditions of the illuminated ROI the desired parameter of the illumination unit can thus be appropriately controlled.

While generally the use of one illumination element as illumination unit is sufficient, according to another embodiment said illumination unit comprises two or more illumination elements (also called light sources). This provides more flexibility in the control of the illumination. Preferably, said two or more illumination elements are arranged at different locations and/or with different orientations. Still further, said two or more illumination elements have different parameters, in particular different wavelengths, intensities and/or illumination angles. Said two or more illumination elements are preferably controlled individually. Said illumination elements may e.g. be LEDs, laser diodes, conventional light bulbs, neon lights, etc. which can be controlled.

Advantageously, said control unit is configured to control said illumination unit based on one or more predetermined parameters. Thus, a user can determine in advance, which parameter(s) is (are) most important for the actual measurement and can thus be used for the control of the illumination unit.

In a practical implementation said control unit is configured to determine the amount of specular reflection in the region of interest and to control said illumination unit based on the determined amount of specular reflection so as to reduce or minimize the amount of specular reflection. Specular reflection has shown to often appear having negative effects on the quality of the obtained vital signs information. This can be improved by taking specular reflection into account in the control of the illumination unit.

If course, other (additional or alternative) parameters may be used for the control, such as the uniformity of illumination in the ROI, good/stable illumination in all relevant channels (wavelengths), no shadow in the ROI, etc.

In another practical implementation said control unit is configured to control said illumination unit based on one or more parameters of a monitored area and/or the derived vital sign information, in particular light intensity of the monitored area, heart rate, oxygen saturation, pulsatility amplitude, pulse shape and/or periodicity of the vital sign information. The monitored area may, for instance, be an area where a patient (e.g. a baby) is arranged within a bed, an incubator or a radiant warmer. Controlling the light intensity may thus be performed in a way ensuring that the region of interest is sufficiently illuminated for deriving vital sign information with sufficient reliability and accuracy, but on the other hand avoiding any unnecessary discomfort to the patient. This may for instance be used to avoid that the face (that may e.g. be the monitored area) or the whole area of the patient is illuminated too much having any negative effects, e.g. on a baby's development.

While generally the use of one detection element as detection unit is sufficient, said detection unit preferably comprises two or more detection elements. Said detection elements are, for instance, image sensors, video camera, RGB camera, infrared camera or still image cameras. While the detection elements generally have identical parameters but are located at different positions and/or with different orientations, in an embodiment the detection elements are different and/or have different parameters so that the detection element resulting in the best vital sign information can be selected for signal evaluation. In still another embodiment the input signals from two or more detection elements may be commonly evaluated, e.g. after averaging the input signals.

Thus, in an embodiment said processing unit is configured to select the input signals generated from light received by the detection element from which vital sign information with the best quality are used for deriving the vital sign information. Further, in an embodiment said processing unit is configured to select the input signals generated from light received by the detection element which received light from the region of interest with the best illumination.

Still further, in an embodiment said detection unit is configured to detect changes of a monitored area, the environment and/or the living being and wherein said control unit is configured, if changes of the monitored area, the environment and/or the living being are detected, to check actual control settings of said illumination unit and to again control said illumination unit based on said input signal and/or said derived vital sign information. Thus, the control can flexibly react to any changes of any measurement conditions.

Finally, in an embodiment said control unit is configured to control said illumination unit to sequentially illuminate said region of interest with (e.g., a processor) different settings of intensity, wavelength, direction and/or illumination angle of light and to select the settings resulting in input signals with the best image quality and/or in vital signs with the best quality. Thus, in a kind of calibration the device can be calibrated initially to find out the best settings of the illumination unit which is then used for the actual measurement.

In another aspect of the present invention a care device is presented comprising:
  a child carrier that carries a newborn,
  a detector that receives light in at least one wavelength interval reflected from at least a region of interest of the and that generates an input signal from the received light,
  a processor that processes the input signal and derives vital sign information of said living being from said input signal by use of remote photoplethysmography,
  an illuminator that illuminates at least said region of interest with light, and
  a controller that controls said illumination unit based on said input signal and/or said derived vital sign information.

In an embodiment said care device is an incubator further comprising a canopy for housing the child and wherein said detector and said illuminator are arranged at said canopy. In another embodiment said care device is a radiant warmer further comprising a radiator that emits radiation for warming the child and wherein said detector, said illuminator and said radiator are arranged at or within a carrier of said radiant warmer. Preferably, said care device is a neonatal care device for caring and obtaining vital sign information of a newborn.

BRIEF DESCRIPTION OF THE DRAWINGS

These and other aspects of the invention will be apparent from and elucidated with reference to the embodiment(s) described hereinafter. In the following drawings FIGS. 3A-3B-3C-3D-3E-3F show images obtained with different illumination settings and reflections appearing in said images, wherein FIGS. 3A-3B-3C show face images of the same subject acquired with three different illumination settings, and wherein FIGS. 3D-3E-3F show the corresponding reflections detected in the images of FIGS. 3A-3B-3C, respectively.

DETAILED DESCRIPTION OF THE INVENTION

Figure 1:
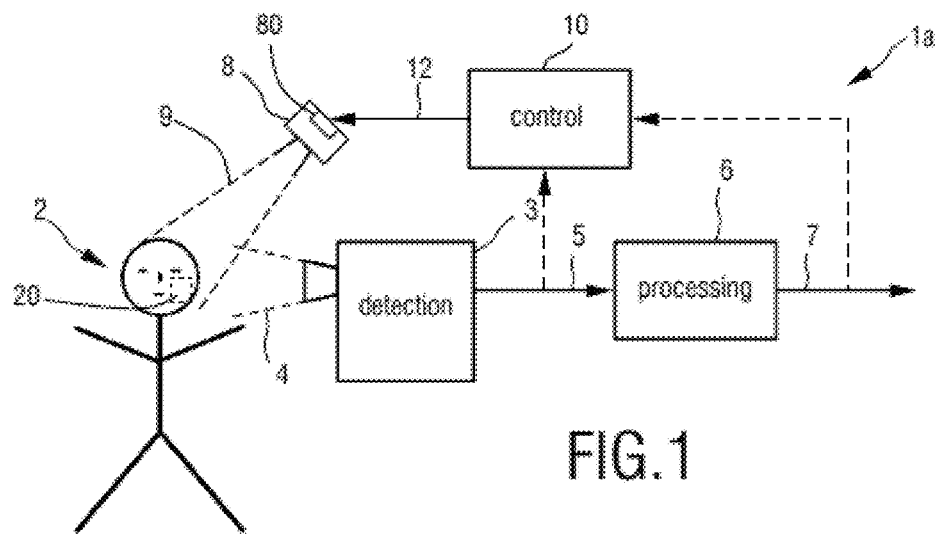
FIG. 1 shows a schematic diagram of a first embodiment of a device for obtaining vital sign information of a living being according to the present invention.

FIG. 1 shows a first embodiment of a device 1a for obtaining vital sign information of a living being 2, e.g. a patient in a hospital, an elderly person monitored in the bed at home, a newborn infants at the NICU or a person doing sports in a fitness club, according to the present invention. The device 1a comprises a detection unit 3 for receiving light 4 in at least one wavelength interval reflected from at least a region of interest of the living being 2 and for generating an input signal 5 from the received light 4. The detection unit 3 is, for instance, configured to register spatio-temporal variations of received light and is preferably an imaging unit for taking images, such as a video camera that substantially continuously or at regular intervals takes images of the living being 2 or at least a region of interest (ROI) 20 of the living being 2.

The device 1a further comprises a processing unit 6 for processing the input signal 5 and deriving vital sign information 7 of said living being 2 from said input signal 5 by use of remote photoplethysmography. The processing unit 6 may e.g. be implemented as software running on a processor or computer, as dedicated hardware or as a mixture of hard- and software. The derivation of vital sign information, e.g. the heartbeat, respiration signal, SpO2 value, hemoglobin value, etc., is generally known in the art, particularly in the field of remote photoplethysmography, e.g. the above cited paper of Wim Verkruysse et al., which explanation is herein incorporated by reference and shall thus not be explained here in more detail.

The obtained vital sign information 7 is then output from the device 1, e.g. transmitted to a central monitoring station (e.g. a monitoring room of a nurse in a hospital) for display on a monitor, directly displayed next to the living being on a display, or transmitted to a remote control center for further processing and/or display.

The device 1a further comprises an illumination unit 8 for illuminating at least said region of interest 20 with light 9. Said illumination unit 8 may comprise one or more light sources which are preferably controllable in brightness and/or frequency spectrum of the emitted light. A practical implementation may comprise an one or more arrays of LEDs with specific wavelengths or wavelength ranges. Other embodiments make use of
- an LED array with wide spectrum combined with spectral filters with different wavelengths, wherein LEDs are switched with the specific filters;
- an LED array with wide spectrum combined with a spectral filter that can adapt its wavelength (electronically/mechanically);
- an LED array with broad spectrum and a rotating disk containing filters with different wavelengths (color wheel) like applied in projectors, wherein the wheel position determines the wavelength used;
- multiple lasers with specific wavelengths;
- an LED array with wide spectrum combined with a spectral filter that can adapt its wavelength (electronically/mechanically);
- an LCD screen or other display where the output signal can be controlled, wherein by adding or replacing frames in the video signal and synchronizing the detection unit (camera) the light conditions can be adapted/controlled.

It shall be noted that more than one illumination unit 8 may also be provided, and that other light sources may be present that provide ambient light or lighting conditions desired by a user, e.g. the room light in a hospital room or changing light in a fitness club.

Finally, the device 1a comprises a control unit 10 for controlling said illumination unit 8 based on said input signal 5 and/or said derived vital sign information 7 through a control signal 12. Thus, vital sign information with optimal quality can be achieved.

Figure 2:
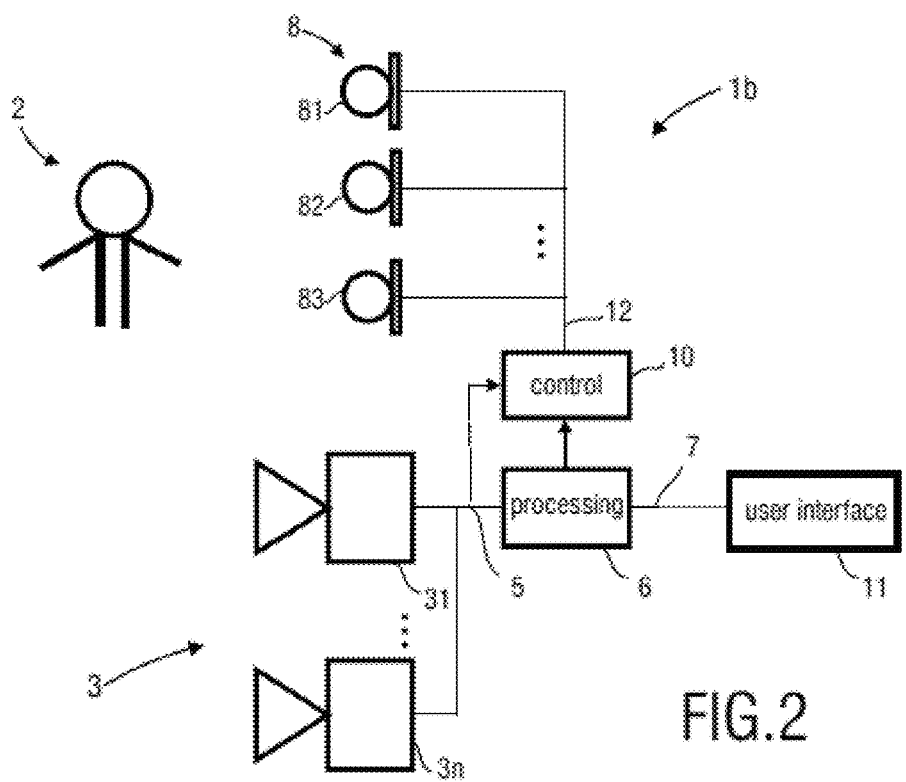
FIG. 2 shows a schematic diagram of a second embodiment of a device for obtaining vital sign information of a living being according to the present invention.

FIG. 2 shows a second embodiment of a device 1b for obtaining vital sign information of a living being 2. The device 1b comprises a detection unit 3 including multiple detection elements 31, . . . , 3n, e.g. n cameras. Further, the device 1b comprises an illumination unit 8 including multiple adjustable illumination elements 81, 82, 83, in particular light sources such as LEDs, and a user interface 11. The cameras 31, . . . 3n are used to visually sense the subject(s) being measured under the illumination. The video signal 5 is processed and analysed in the processor 6 to derive the vital sign information 7 (e.g., an SpO2 signal), which can be visualized in the user interface 11, such as a display. The multiple illumination elements 81, 82, 83, are placed at different locations and/or with different angles and are controlled by the control unit 10, based on the camera signal 5 and/or the derived vital sign information 7.

For camera-based vital sign measurement, one or multiple regions of interest are selected in the skin area (manually or automatically), preferably before the measurement, e.g., in the forehead or cheek. Two ROIs are illustrated in FIGS. 3A-3F.

In an embodiment, before starting measurement, the illumination unit will be configured automatically. For instance, individual illumination elements and combinations of them are switched on (with different levels) and off sequentially. The acquired images with different illumination settings are then analysed by the processor, and the optimal illumination setting is selected and adjusted based on the analysis on the imaging data (i.e. the input signal generated from the received light) and/or the derived vital sign information.

In an embodiment, the specular reflection in the ROI is used as one of criterion, that is, the illumination that causes no or little reflections in the ROI is selected. Reflection can be detected with a generally known video analysis algorithm.

Figures 3A, 3B, 3C:
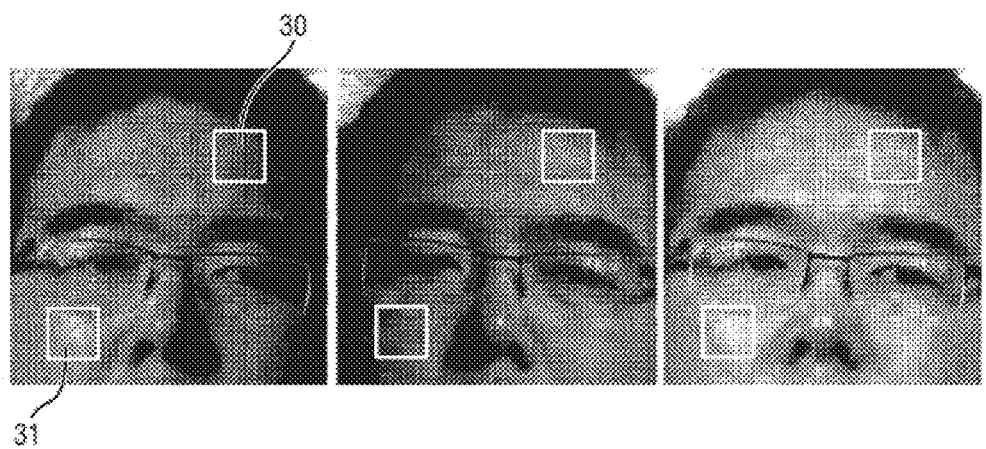
Figures 3D, 3E, 3F:
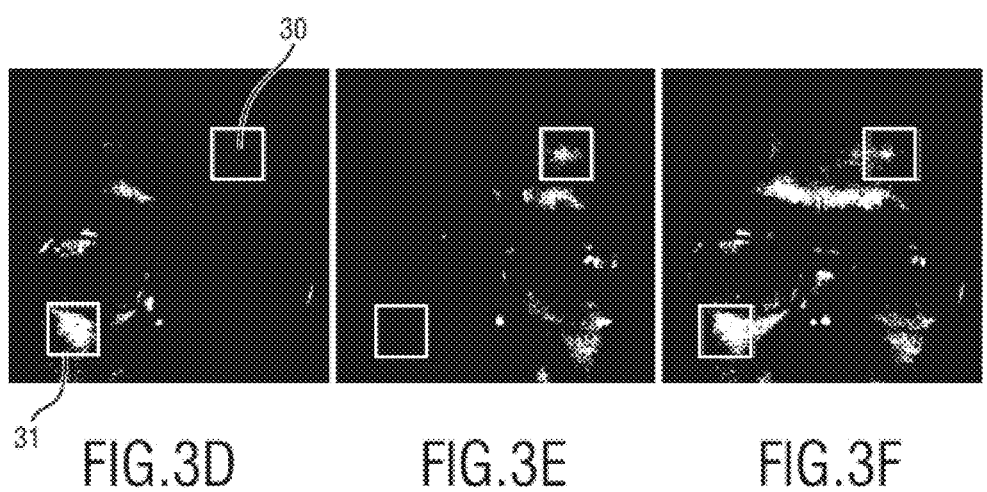

FIGS. 3A-3C show face images of the same subject acquired with three different illumination settings and FIGS. 3D-3F show the corresponding reflections detected in these images. Two example ROIs are considered here. Apparently, if the top-right ROI 30 is used, the illumination setting used for obtaining FIGS. 3A and 3D is selected; if the bottom-left ROI 31 is used, the illumination setting used for obtaining FIGS. 3B and 3E is selected.

Other factors can also be considered in the criterion, for example the uniformity of illumination in the ROI, good/stable illumination in all relevant channels (wavelengths) and/or no shadow in the ROI.

Besides the imaging quality, the property or quality of the derived vital sign information from the ROI (such as PPG signal or SpO2 signal) can also be used as criterion to select and adjust the illumination, for example reasonable heart rate (e.g., 30-250 bpm) and oxygen saturation (50-100%

SpO2 in all cases, 95-100% in 99% of the cases), the pulsatility amplitude, the pulse shape and/or the periodicity of PPG signal.

To reduce disturbance (to the user) and time of the illumination self-configuration process, multiple cameras, placed at different locations and/or with different angles, are used in an embodiment. For one illumination, the acquired images of different cameras will be analysed. If any of these cameras gets the optimal illumination, the camera (and the illumination) will be used for measurement. With multiple cameras, it is easier and faster to find the optimal illumination.

After changes in the environment, the living being and/or the measurement arrangement (e.g., re-selecting ROI, subject moving), the illumination and cameras can be assessed, and, if necessary, are re-adjusted or re-selected.

In the following, another field of application of the present invention will be examined.

Premature babies are leaving the protected environment in the uterus before ready for the earth. They are not ready in many areas. Neonatal Intensive Care Units (NICUs) are prepared to take care of the special needs of preemies but still suffer from many disadvantages. The intensive care has to perform a lot of tasks in a way and with equipment that is obtrusive to the baby and has negative impact on getting healthy and mature. In no way is this close to what a fetus is experiencing the mother's womb.

An example is the need to monitor vital signs and stick electrodes or sensors on the fragile baby's skin. The skin often gets peeled off when the parts need to be changed. All these sensing parts are usually clumsy when compared to the size of these very small children. The parts prevent or interrupt a good sleep. Current practice in NICU in mature markets is to follow the so-called developmental care as e.g. described in "Developmental Care of Newborns and Infants, A Guide for Health Professionals", Editors: Carole Kenner, Jacqueline M McGrath, National Association of Neonatal Nurses, 2010.

The present invention can be used to support this effort. Further, the present invention can help to protect the baby from excess light and from sensors applied to the skin and to improve parent contact through camera while keeping the premature baby as protected as it can from the outside world. The present invention can also overcome the problem of bulky equipment that makes camera use practically impossible today.

In the following various embodiments of the present invention will be explained how the detection unit (e.g. in the form of a camera) and the illumination unit can be best integrated into the NICU environment. Generally, but particularly in such an environment, the use of camera may serve for various purposes including monitoring of the baby's vital signs, parent-child bonding and remote care.

As mentioned above a premature baby needs to be protected from too much light. The ideal place for the fetus was mother's womb where there is very little light from outside. Still, the premature baby needs lot of care, treatment and procedures to support its life and growth. A camera with integrated light that is optimally mounted close to the baby could help to mimic the womb environment as close as possible. Still a camera can help interfacing to the baby for the caregivers and parents. Thus, dedicated and minimal lighting can be used
i) for visual inspection of the baby, look at eyes, at movements;
ii) make parents see the baby while keeping it covered; and
iii) monitoring vital signs of the baby.

Vital signs monitoring requires some level of light on the baby. The amount and quality of room light in a NICU is neither well defined nor constant. There are many times when the baby sleeps. Dimming lights are a must to provide best developmental care. This is often achieved by covering the incubator with a blanket and switching off room light. This may lead to situations where the light levels become inappropriate for the detection unit (e.g. a video sensor of a camera) and the signal to noise level gets unacceptably low. The quality of the received light (e.g. a video image) becomes too bad for watching or further processing, i.e. it becomes useless for its intended purpose. Also, the wavelength distribution of the illumination may not be appropriate for the camera (monitoring) purpose.

Therefore a level controlled illumination unit (e.g. light source), preferably at the detection unit (e.g. at the camera) is proposed that provides adequate intensity at the wavelengths needed for the purpose and at the same time does not unnecessarily discomfort the baby by keeping it a low as possible.

Figure 4:
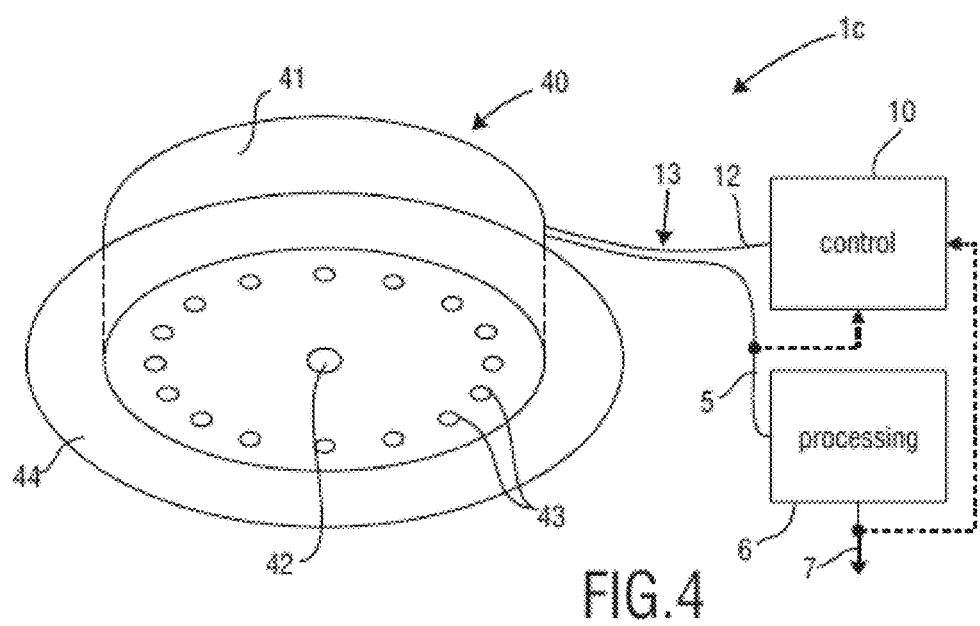
FIG. 4 shows a schematic diagram of a third embodiment of a device for obtaining vital sign information of a living being according to the present invention.

FIG. 4 shows a schematic diagram of a third embodiment of a device 1c for obtaining vital sign information of a living being according to the present invention. In this embodiment an integrated camera frontend 40 including illumination lighting is used, which is connected to the processor 6 and the controller 10 via a cable 13 including signal lines for transmitting the input signals 5 and the control signals 12.

The integrated camera frontend 40 comprises a frontend housing 41, a camera lens 42 (behind which the camera (not shown) is arranged inside the housing, a plurality of illumination LEDs 43 and a soft suction cup ring for attaching the integrated camera frontend 40 to an incubator or other device.

In another embodiment a spot light source close to the camera is used to avoid shadows on the image and to keep the location of the field of view of camera and light small. In still another embodiment the light source is made large in area and diffuse in order to minimize the chance to create shades and block the light.

The light levels can be controlled by feedback of the processor 6 using the image intensity at one or more wavelength ranges. While in typical studio setups the light levels are maximized to get the best pictures it is desired in such an application to use the minimum light levels with the premature babies to conform to their development needs and mimic the dim environment in the uterus. The minimum is specific to the purpose of the camera use. Thus, for instance the light level in a monitoring area (comprising the premature baby or at least the baby's face) is monitored and used to control the light level of the illumination unit.

In addition the color (wavelength) of the light could be tuned to the purpose and chosen so it has the least visual sensitivity for the human eye. For instance, if the camera is used for respiration monitoring where motion of the chest is the key interest then red or even near infrared light is preferably used.

As shown in FIG. 4, the illumination unit is implemented by a set of LEDs, with the wavelengths selected according to the need of the monitoring goal. For pulse monitoring, where the change in skin color is used, there would be a need of LEDs in the green range (e.g. 500 nm) and a reference in the red range (e.g. 650 nm). If the camera is used to measure bilirubin levels via skin several wavelengths need to be covered to make the calculations (e.g. 460 nm, 520 nm, 650 nm).

In this embodiment the illumination elements 43 (e.g. LEDs or lights) are arranged in a circle around the camera as a ring light. Preferably, the illumination cone matches the field of view of the camera for best energy use and avoids reflections and glare to caregivers and the patient as well as light interference with similar systems close by.

In another approach, in which widely diffused lights are used, glowing surfaces surrounding the baby are used. This could be achieved by any sort of conventional spatially spread light sources as fluorescence bulbs including diffusers or newer OLED technologies that have the intrinsic properties of emitting light over a larger surface. They may be embedded in the transparent side and top walls of an incubator canopy.

The camera frontend 41 is preferably mounted in a way, where obstruction of the camera view does not likely occur due to any circumstances that are likely to happen in the NICU care. A good position is defined where the monitored are, e.g. the interesting body part like the face, is in good view and where external room light can still be shielded to protect the baby's sleep without affecting the intended camera functionality.

Figure 5:
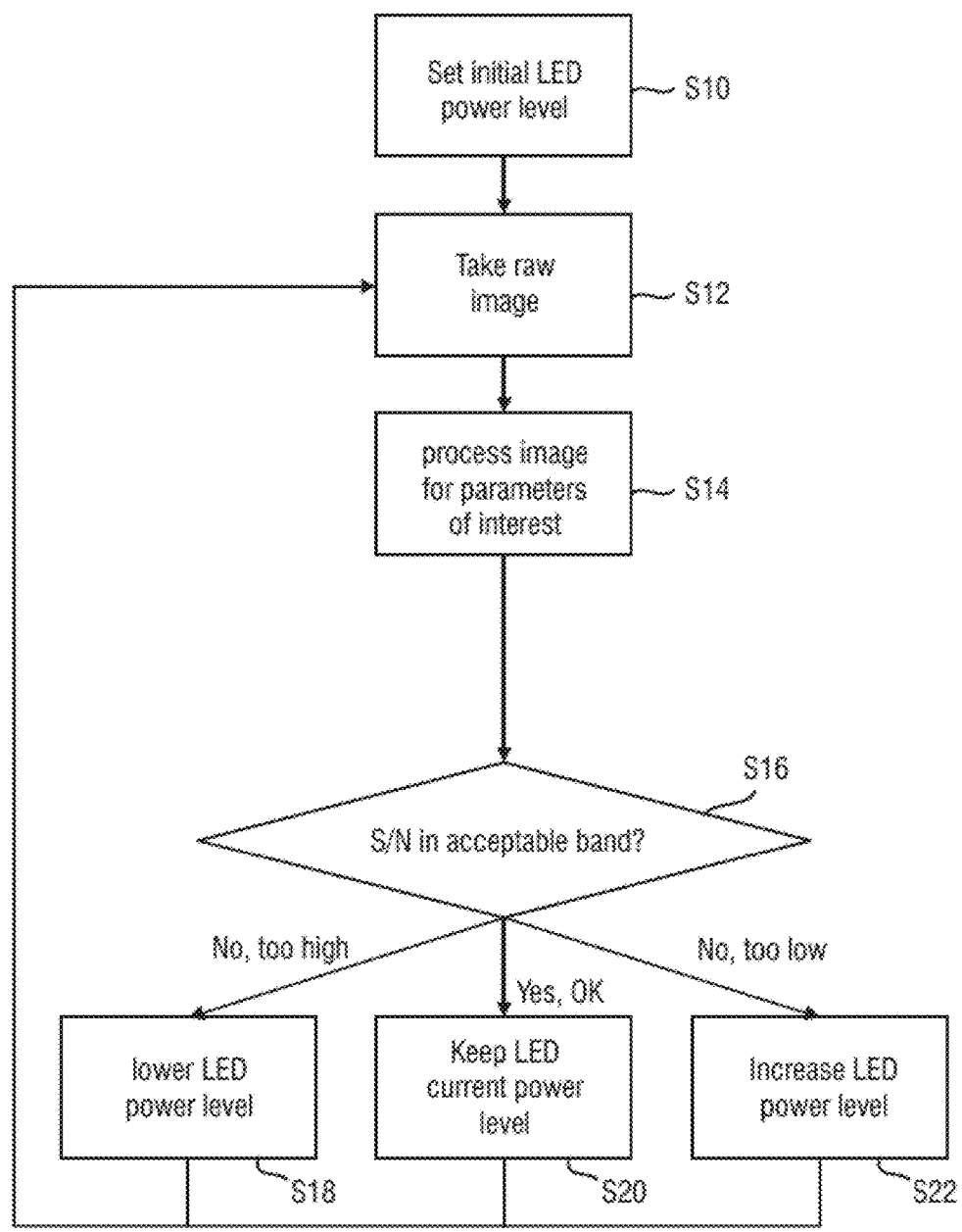
FIG. 5 shows a flowchart of an embodiment of a method according to the present invention.

The power of the different illumination elements 43 (e.g. LEDs) can be controlled independently to achieve the optimal tradeoff between signal-to-noise ratio and least baby illumination intensity. A flowchart corresponding of a corresponding method is shown in FIG. 5. In a first step S10 the initial LED power level is set. In a second step S12 a raw image (as input signal) is taken, in a third step S14 the image is processed to obtain the desired information (e.g. a desired vital sign). In a fourth step S16 it is checked if the SNR is in an acceptable range. Depending on the result of this check the LED power level is lowered (S18), kept stable (S20) or increased (S22). Thereafter the method returns to step S12.

Figure 6:
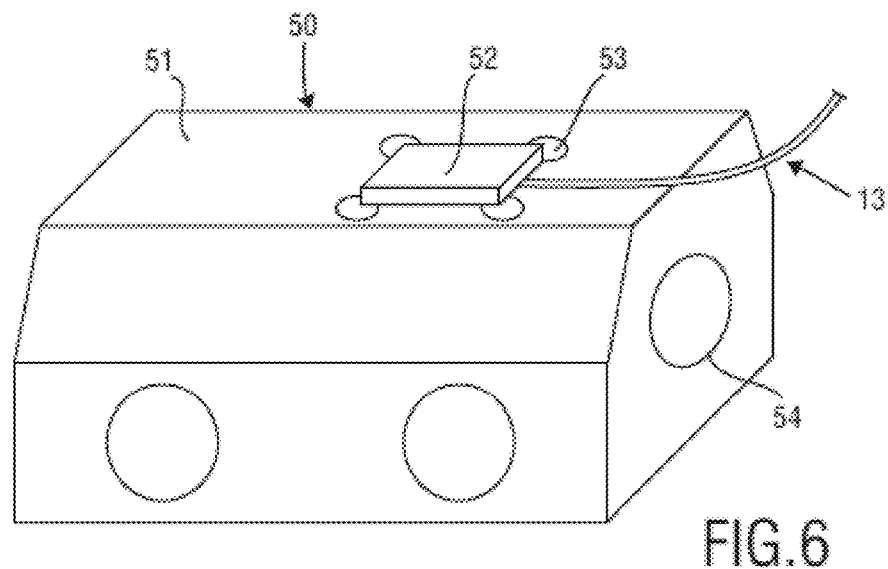
FIG. 6 shows the arrangement of the illumination unit and the detection unit of a device according to the present invention at an incubator.

FIG. 6 shows an incubator 50 including a device according to the present invention. Very small and fragile babies are typically kept in such a closed incubator 50 that allows for a controlled humidity and temperature environment. The baby's bed is covered with a transparent canopy 51 that has opening holes 54 and doors to get access to the patient. For such an incubator a good place to put the integrated camera frontend 52 is on top of the canopy 51, which has in most cases a flat top.

The integrated camera frontend 52 may be mounted inside or outside of the canopy 51. In order to hold it in place a suction cup 53 is preferably used to fix it inside or outside or make it heavy enough and use gravity with a non-slippery surface to the canopy 51 to stay in place outside. If outside the suction cup 53 or non-slip ring (44, see FIG. 4) may be formed as kind of opaque rubber seal that also keeps stray light away from outside. Close contact of the optical camera and light surfaces to the canopy 51 also keeps dust and contamination away.

If, for some reason the integrated camera frontend 52 needs to be inside the canopy 51, e.g. because of excess absorption of the light intended to measure, a secure way of fixing it in the middle of the compartment on the top over the baby is needed. It could be a cup like compartment with a transparent window to the baby. The window can be made of materials and thickness better suited transparent for all the wavelengths needed than the canopy is made off.

For some applications like parent bonding or sound monitoring a microphone can be included in the integrated camera frontend 52. In this case there is preferably an opening or acoustical membrane that allows sound waves to pass while keeping contamination and water away from the integrated camera frontend 52.

Direct mounting on or in the incubator 50 also gives better mechanical stability, i.e. less shaky pictures compared to mounting on separate arms or stands. It still allows the caregivers to cover the incubator by blankets to protect the baby from external light.

Figure 7:
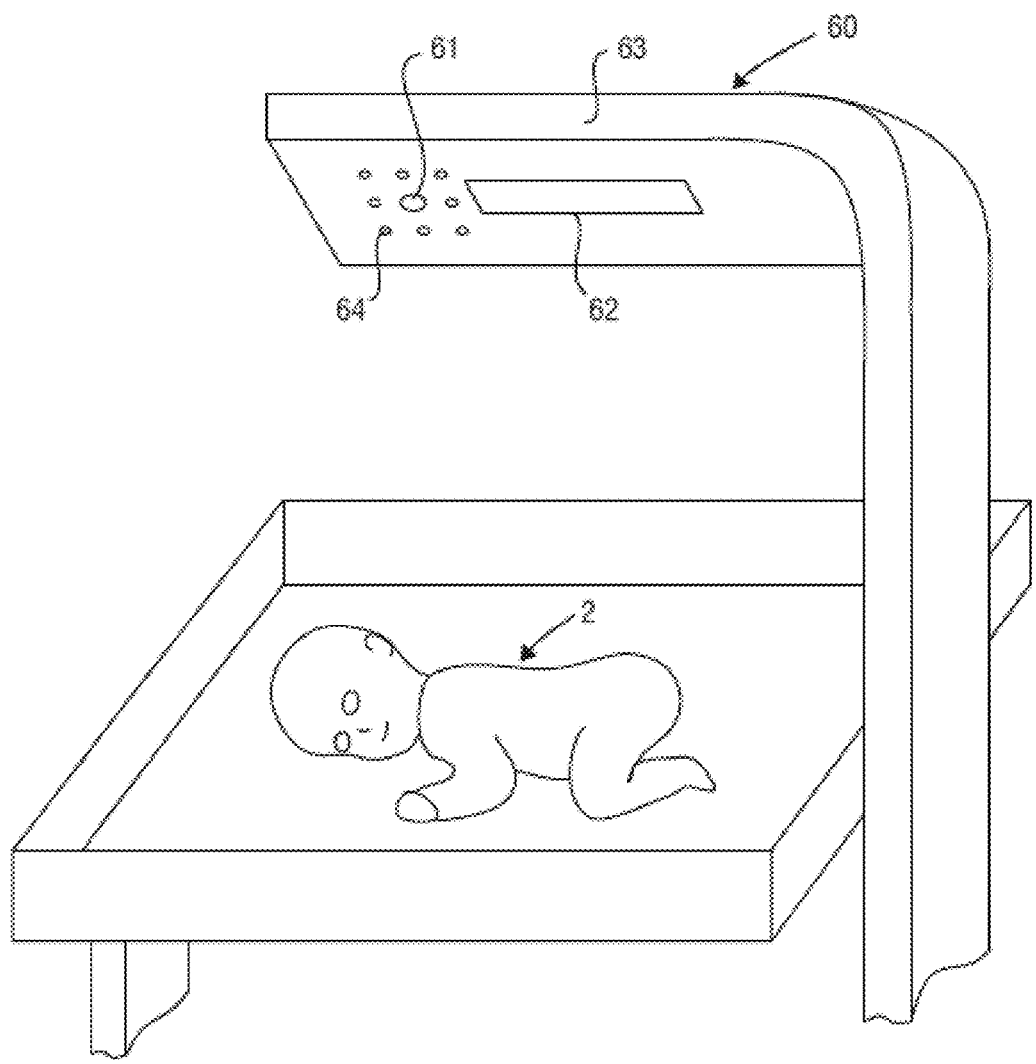
FIG. 7 shows the arrangement of the illumination unit and the detection unit of a device according to the present invention in a radiant warmer.

FIG. 7 shows a radiant warmer 60 including a device according to the present invention. Larger and closer to term babies are often kept in such a radiant warmer 60 to help keep the temperature regulated. This gives better access to the patient for treatment, care and procedures. But still the baby is at a well-defined spot and a camera 3 can be mounted at a predefined position.

A radiant warmer 60 normally has an IR warming lamp 62 centered above the baby 2. The means to hold that heating element 62 makes it also the ideal place to integrate the integrated camera frontend along with this heating element 62 at the same spot as much a as space allows. The arm 63 that carries the heating element 62 can also carry the camera 61 inside (basically invisible as it only need a little hole), and it could also contain the illumination elements 64 to support the camera 61. Cable routing can be managed there perfectly inside the warmer, in particular the arm 63, if the processor, the control unit and a display for the camera parameters, the control and the results is also integrated in the radiant warmer 60. The radiant warmer 60 may share the user interface and any computation means between the monitoring and the warming functions.

The advantage of this arrangement over an integrated camera frontend on a separate arm is that it is unobtrusive, nearly invisible and well protected from contamination due to fluid spills and provides better access to the baby due to less equipment and rood cable management.

In summary, the latter embodiments provide controlled light levels by a feedback loop from the processing of detected signals, dedicated wavelengths to optimize the purpose of the camera and at the same time be least disturbing to the baby, and an improved workflow with incubators and warmers through integration of camera and lighting.

Thus, according to these latter embodiments of the present invention a care device is presented as described above.

As described in an embodiment said care device is an incubator further comprising a canopy for housing the child and wherein said detector and said illuminator are arranged at said canopy. In another embodiment said care device is a radiant warmer further comprising a radiator that emits radiation for warming the child and wherein said detector, said illuminator and said radiator are arranged at or within a carrier of said radiant warmer. Preferably, said care device is a neonatal care device for caring and obtaining vital sign information of a newborn.

The present invention may be applied in various applications. Heart rate, breathing rate, and SpO2 are very relevant factors in patient monitoring and home-healthcare where remote heart rate monitoring becomes more and more relevant. Further, the present invention may be applied to register heartbeat in fitness devices. The proposed invention can particularly be applied in any application where camera-based vital signs monitoring is performed with controllable illumination that is changing or with variable light conditions. Normally, the vital signs extraction is extremely challenging and even impossible in some cases, but can now be accurately and reliably achieved.

Furthermore, the different embodiments can take the form of a computer program product accessible from a computer usable or computer readable medium providing program code for use by or in connection with a computer or any device or system that executes instructions. For the purposes of this disclosure, a computer usable or computer readable medium can generally be any tangible device or apparatus that can contain, store, communicate, propagate, or transport the program for use by or in connection with the instruction execution device.

In so far as embodiments of the disclosure have been described as being implemented, at least in part, by software-controlled data processing devices, it will be appreciated that the non-transitory machine-readable medium carrying such software, such as an optical disk, a magnetic disk, semiconductor memory or the like, is also considered to represent an embodiment of the present disclosure.

The computer usable or computer readable medium can be, for example, without limitation, an electronic, magnetic, optical, electromagnetic, infrared, or semiconductor system, or a propagation medium. Non-limiting examples of a computer readable medium include a semiconductor or solid state memory, magnetic tape, a removable computer diskette, a random access memory (RAM), a read-only memory (ROM), a rigid magnetic disk, and an optical disk. Optical disks may include compact disk-read only memory (CD-ROM), compact disk-read/write (CD-R/W), and DVD.

Further, a computer usable or computer readable medium may contain or store a computer readable or usable program code such that when the computer readable or usable program code is executed on a computer, the execution of this computer readable or usable program code causes the computer to transmit another computer readable or usable program code over a communications link. This communications link may use a medium that is, for example, without limitation, physical or wireless.

A data processing system or device suitable for storing and/or executing computer readable or computer usable program code will include one or more processors coupled directly or indirectly to memory elements through a communications fabric, such as a system bus. The memory elements may include local memory employed during actual execution of the program code, bulk storage, and cache memories, which provide temporary storage of at least some computer readable or computer usable program code to reduce the number of times code may be retrieved from bulk storage during execution of the code.

Input/output, or I/O devices, can be coupled to the system either directly or through intervening I/O controllers. These devices may include, for example, without limitation, keyboards, touch screen displays, and pointing devices. Different communications adapters may also be coupled to the system to enable the data processing system to become coupled to other data processing systems, remote printers, or storage devices through intervening private or public networks. Nonlimiting examples are modems and network adapters and are just a few of the currently available types of communications adapters.

The description of the different illustrative embodiments has been presented for purposes of illustration and description and is not intended to be exhaustive or limited to the embodiments in the form disclosed. Many modifications and variations will be apparent to those of ordinary skill in the art. Further, different illustrative embodiments may provide different advantages as compared to other illustrative embodiments. The embodiment or embodiments selected are chosen and described in order to best explain the principles of the embodiments, the practical application, and to enable others of ordinary skill in the art to understand the disclosure for various embodiments with various modifications as are suited to the particular use contemplated. Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality. A single element or other unit may fulfill the functions of several items recited in the claims. The mere fact that certain measures are recited in mutually different dependent claims does not indicate that a combination of these measures cannot be used to advantage.

The invention claimed is:

1. A device for obtaining vital sign information of a living being, comprising:
    a detector that receives light in at least one wavelength interval reflected from at least a region of interest of a living being and that generates an input signal from the received light,
    an illuminator that illuminates at least said region of interest with light, and
    a processor that processes the input signal and derives vital sign information of said living being from said input signal by use of remote photoplethysmography and that controls said illuminator based on said input signal and/or said derived vital sign information,
    wherein said control of said illuminator comprises one or more changes to one or more parameters of the illuminator, the one or more parameters of the illuminator comprising intensity, wavelength, direction, and/or illumination angle of the light emitted by said illuminator.

2. The device as claimed in claim 1, wherein said illuminator comprises two or more illuminators.

3. The device as claimed in claim 2, wherein said two or more illuminators are arranged at different locations and/or with different orientations.

4. The device as claimed in claim 2, wherein said two or more illuminators have different parameters, in particular different wavelengths, intensities, and/or illumination angles.

5. The device as claimed in claim 3 or 4, wherein said processor is configured to individually control said two or more illuminators.

6. The device as claimed in claim 1, wherein said processor is configured to determine the amount of specular reflection in the region of interest and wherein the change of the one or more parameters of said illuminator is based on the determined amount of specular reflection so as to reduce or minimize the amount of specular reflection.

7. The device as claimed in claim 1, wherein said control of said illuminator further comprises one or more changes to one or more parameters of a monitored area and/or the derived vital sign information, in particular light intensity of the monitored area, heart rate, oxygen saturation, pulsatility amplitude, pulse shape, and/or periodicity of the vital sign information.

8. The device as claimed in claim 1, wherein said detector comprises two or more detectors.

9. The device as claimed in claim 8, wherein said processor is configured to select the input signals generated from light received by the detectors from which vital sign information with the best quality are used for deriving the vital sign information.

10. The device as claimed in claim 8, wherein said processor is configured to select the input signals generated from light received by the detector which received light from the region of interest with the best illumination.

11. The device as claimed in claim 1, wherein said detector is configured to detect changes of a monitored area, the environment, and/or the living being and wherein said processor is configured, if changes of the monitored area, the environment, and/or the living being are detected, to check the one or more parameters of said illuminator and to again change the one or more parameters of said illuminator based on said input signal and/or said derived vital sign information.

12. The device as claimed in claim 1, wherein said control of said illuminator further comprises one or more changes to the one or more parameters of the illuminator to sequentially illuminate said region of interest with different settings of intensity, wavelength, direction, and/or illumination angle of light and to select the settings resulting in input signals with the best image quality and/or vital signs with the best quality.

* * * * *